(12) United States Patent
Williams et al.

(10) Patent No.: US 11,969,298 B2
(45) Date of Patent: Apr. 30, 2024

(54) LOCKOUT MECHANISMS FOR SURGICAL INSTRUMENTS

(71) Applicant: Covidien LP, Mansfield, MA (US)

(72) Inventors: Justin Williams, Southbury, CT (US); Joseph Eisinger, Northford, CT (US); Michael Ingmanson, Stratford, CT (US); Kelly Azeredo, Killingworth, CT (US); Thomas Wingardner, North Haven, CT (US); David Valentine, Jr., Hamden, CT (US)

(73) Assignee: COVIDIEN LP, Mansfield, MA (US)

( * ) Notice: Subject to any disclaimer, the term of this patent is extended or adjusted under 35 U.S.C. 154(b) by 115 days.

(21) Appl. No.: 17/862,941

(22) Filed: Jul. 12, 2022

(65) Prior Publication Data

US 2022/0338951 A1 Oct. 27, 2022

Related U.S. Application Data

(63) Continuation of application No. 16/684,718, filed on Nov. 15, 2019, now Pat. No. 11,389,263.
(Continued)

(51) Int. Cl.
*A61B 17/072* (2006.01)
*A61B 17/068* (2006.01)
(Continued)

(52) U.S. Cl.
CPC ............ *A61B 90/03* (2016.02); *A61B 17/068* (2013.01); *A61B 17/07207* (2013.01);
(Continued)

(58) Field of Classification Search
CPC ................ A61B 17/068; A61B 17/072; A61B 17/07207; A61B 17/115; A61B 17/1155;
(Continued)

(56) References Cited

U.S. PATENT DOCUMENTS 3,388,847 A 6/1968 Kasulin et al.
3,552,626 A 1/1971 Astafiev et al.
(Continued)

FOREIGN PATENT DOCUMENTS

CA 908529 A 8/1972
CA 2805365 A1 8/2013
(Continued)

OTHER PUBLICATIONS

Chinese Office Action dated Jun. 13, 2023 for Chinese Patent Application No. 201911250682.0 (14 pages).
(Continued)

*Primary Examiner* — Scott A Smith
(74) *Attorney, Agent, or Firm* — Carter, DeLuca & Farrell, LLP

(57) ABSTRACT

Surgical instruments include a first drive assembly having a first drive gear and a lockout mechanism positioned for releasable engagement with the first drive assembly to inhibit rotation of the first drive gear. The lockout mechanism includes a pawl and an actuator means for moving the pawl from a first position in engagement with the first drive gear to a second position spaced from the first drive gear.

20 Claims, 11 Drawing Sheets

Related U.S. Application Data

(60) Provisional application No. 62/779,187, filed on Dec. 13, 2018.

(51) Int. Cl.
   *A61B 90/00* (2016.01)
   *A61B 17/00* (2006.01)
   *A61B 17/115* (2006.01)
   *A61B 17/29* (2006.01)
   *A61B 17/295* (2006.01)

(52) U.S. Cl.
   CPC ........... *A61B 2017/00407* (2013.01); *A61B 2017/00477* (2013.01); *A61B 17/072* (2013.01); *A61B 2017/07214* (2013.01); *A61B 2017/07257* (2013.01); *A61B 2017/07285* (2013.01); *A61B 17/115* (2013.01); *A61B 2017/2943* (2013.01); *A61B 2017/2946* (2013.01); *A61B 17/295* (2013.01); *A61B 2090/035* (2016.02)

(58) Field of Classification Search
   CPC ........... A61B 2017/00473; A61B 2017/00477; A61B 2017/07214; A61B 2017/07228
   USPC .............. 227/19, 175.1, 175.2, 176.1, 180.1; 606/1, 139, 153, 219
   See application file for complete search history.

(56) References Cited

U.S. PATENT DOCUMENTS

| | | |
|---|---|---|
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filip |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |

(56) References Cited

U.S. PATENT DOCUMENTS

| | | |
|---|---|---|
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |

(56) References Cited

U.S. PATENT DOCUMENTS

| | | |
|---|---|---|
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 9,023,014 B2 | 5/2015 | Chowaniec et al. |
| 9,055,943 B2 | 6/2015 | Zemlok et al. |
| 9,554,803 B2 | 1/2017 | Smith et al. |
| 9,700,310 B2 | 7/2017 | Morgan et al. |
| 11,389,263 B2 * | 7/2022 | Williams ............. A61B 17/068 |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000867 A1 * | 1/2006 | Shelton, IV ..... A61B 17/07207 227/19 |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0206130 A1 * | 8/2009 | Hall ....................... A61B 50/30 227/175.2 |

(56) References Cited

U.S. PATENT DOCUMENTS

| | | |
|---|---|---|
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0054261 A1* | 3/2011 | Battles ............... A61B 17/3462 600/210 |
| 2011/0114697 A1 | 5/2011 | Baxter, III et al. |
| 2011/0114700 A1 | 5/2011 | Baxter et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0116262 A1 | 5/2012 | Houser et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2015/0157321 A1 | 6/2015 | Zergiebel et al. |
| 2016/0106406 A1 | 4/2016 | Cabrera et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2016/0361057 A1 | 12/2016 | Williams |
| 2016/0374667 A1 | 12/2016 | Miller |
| 2017/0086879 A1 | 3/2017 | Williams |
| 2017/0128068 A1 | 5/2017 | Zhang et al. |
| 2020/0188053 A1* | 6/2020 | Williams ........... A61B 17/1155 |

FOREIGN PATENT DOCUMENTS

| | | |
|---|---|---|
| CN | 106455936 A | 2/2017 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3103402 A1 | 12/2016 |
| EP | 3108824 A1 | 12/2016 |
| EP | 3245959 A2 | 11/2017 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 2008107918 A1 | 9/2008 |

OTHER PUBLICATIONS

Partial European Search report dated Apr. 17, 2020, issued in EP Appln. No. 19215513, 15 pages.
European Search Report dated Aug. 28, 2020, corresponding to counterpart European Application No. 19215513.3; 14 pages.
European Search Report dated Nov. 15, 2021, corresponding to counterpart European Application No. 21203364.1; 11 pages.

* cited by examiner

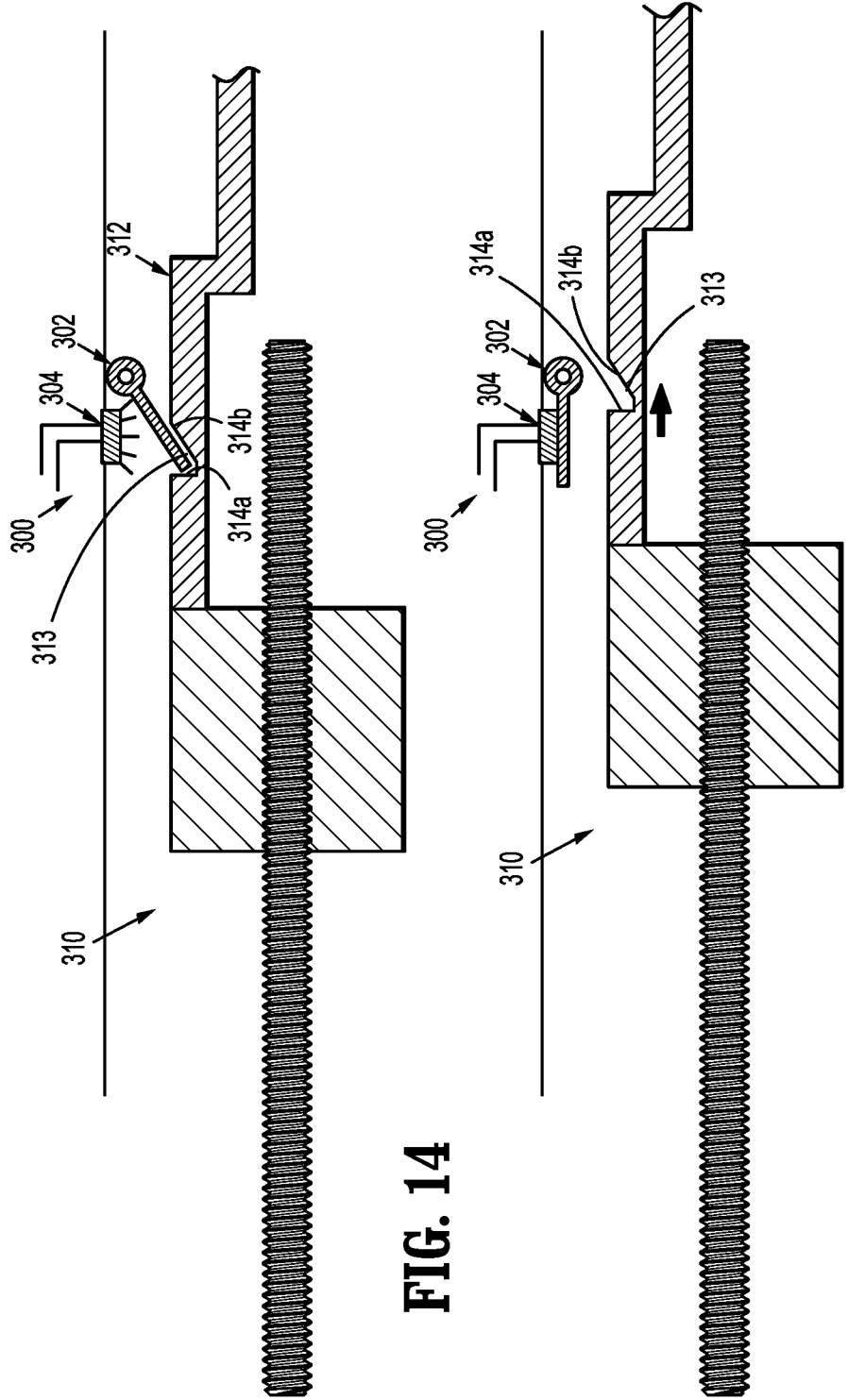

LOCKOUT MECHANISMS FOR SURGICAL INSTRUMENTS

CROSS-REFERENCE TO RELATED APPLICATION

This application is a continuation application of U.S. patent application Ser. No. 16/684,718 filed Nov. 15, 2019, now U.S. Pat. No. 11,389,263, which claims the benefit of and priority to U.S. Provisional Patent Application Ser. No. 62/779,187 filed Dec. 13, 2018, the entire content of each of which is hereby incorporated by reference herein.

FIELD

The present disclosure relates to surgical instruments. More particularly, the present disclosure relates to lockout mechanisms for surgical instruments.

BACKGROUND

Surgical instruments for, e.g., applying staples, clips, or other fasteners to tissue, are well known. Generally, surgical instruments include an actuation unit, e.g., a handle assembly for actuating the instrument, an elongate shaft for accessing a body cavity, and a tool assembly disposed at a distal end of the elongate shaft. The surgical instruments may be manual or powered. Typically, one or more drive assemblies extend from the handle assembly, through the elongate shaft of the surgical instrument for effecting at least one function of the end effector, e.g., clamping, stapling, or cutting.

It would be beneficial to have a surgical instrument with one or more mechanical lockout mechanisms to inhibit operation of the surgical instrument prior to certain conditions being met and/or to prevent a second or subsequent operation of the surgical instrument.

SUMMARY

According to an aspect of the present disclosure, a surgical instrument is provided. The surgical instrument includes a first drive assembly including a first drive gear; and a lockout mechanism positioned for releasable engagement with the first drive assembly to inhibit rotation of the first drive gear. The lockout mechanism includes a pawl and an actuator means for moving the pawl from a first position in engagement with the first drive gear to a second position spaced from the first drive gear.

In embodiments, the pawl includes a plurality of teeth and the first drive gear includes a plurality of teeth. The plurality of teeth of the pawl may engage the plurality of teeth of the first drive gear when the pawl is in the first position. The pawl may pivot from the first position to the second position. The surgical instrument may further include an adapter assembly. The first drive assembly and the lockout mechanism may be disposed within the adapter assembly. The actuator may include a motor, a servo, or an electromagnet.

The surgical instrument may further include a handle assembly. The adapter assembly may be releasably secured to the handle assembly. In addition, the surgical instrument may further include an end effector releasably secured to the adapter assembly. The end effector may include a loading unit and an anvil assembly.

Also provided is a surgical instrument including an elongate body, a drive member received within the elongate body, a trocar assembly releasably receivable within the elongate body, and a retaining mechanism for releasably securing the trocar assembly within the elongate body. The drive member includes a flange and is movable between a retracted position and an advanced position. The trocar assembly includes a trocar housing defining first and second opposed openings. The retaining mechanism includes a cam wire including a free end and is moveable between a locked position and an unlocked position. When the cam wire is in the locked position, the free end of the cam wire obstructs a path of the flange of the drive member to inhibit movement of the drive member to the advanced position.

In embodiments, the retaining mechanism further includes first and second retaining members moveably positioned about the cam wire. The first and second retaining members may be releasably receivable within the first and second opposed openings of the trocar housing when the trocar assembly is seated within the elongate body. The cam wire may be in the unlocked position when the first and second retaining members are received within the first and second opposed openings in the trocar housing. The cam wire may be in the locked position when the first and second retaining members engage the trocar housing.

The retaining mechanism of the surgical instrument may further include a release button for moving the cam wire between the unlocked position and the locked position. The retaining mechanism may further include a retaining block through which the trocar assembly is received. The free end of the cam wire may extend from the retaining block when the cam wire is in the locked position. The free end of the cam wire may be disposed within the retaining block when the cam wire is in the unlocked position.

In addition, a surgical instrument is provided that includes a drive member including a cutout defined by a distal facing surface, and a lockout mechanism disposed adjacent to the drive member. The lockout mechanism includes a locking member pivotally secured relative to the drive member and moveable from a first position in engagement with the distal facing surface of the drive member and a second position spaced from the distal facing surface of the drive member, the drive member being moveable from the first position to the second position by an electromagnet.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 14 is a partial cross-sectional side view of a lockout mechanism according to another embodiment of the present disclosure, with a plunger member in a locked position;

FIG. 15 is a partial cross-sectional side view of the lockout mechanism shown in FIG. 14, with the plunger member in an unlocked position;

FIG. 16 is a partial cross-sectional side view of a drive member of the lockout mechanism shown in FIGS. 14 and 15;

DETAILED DESCRIPTION

Figure 1:
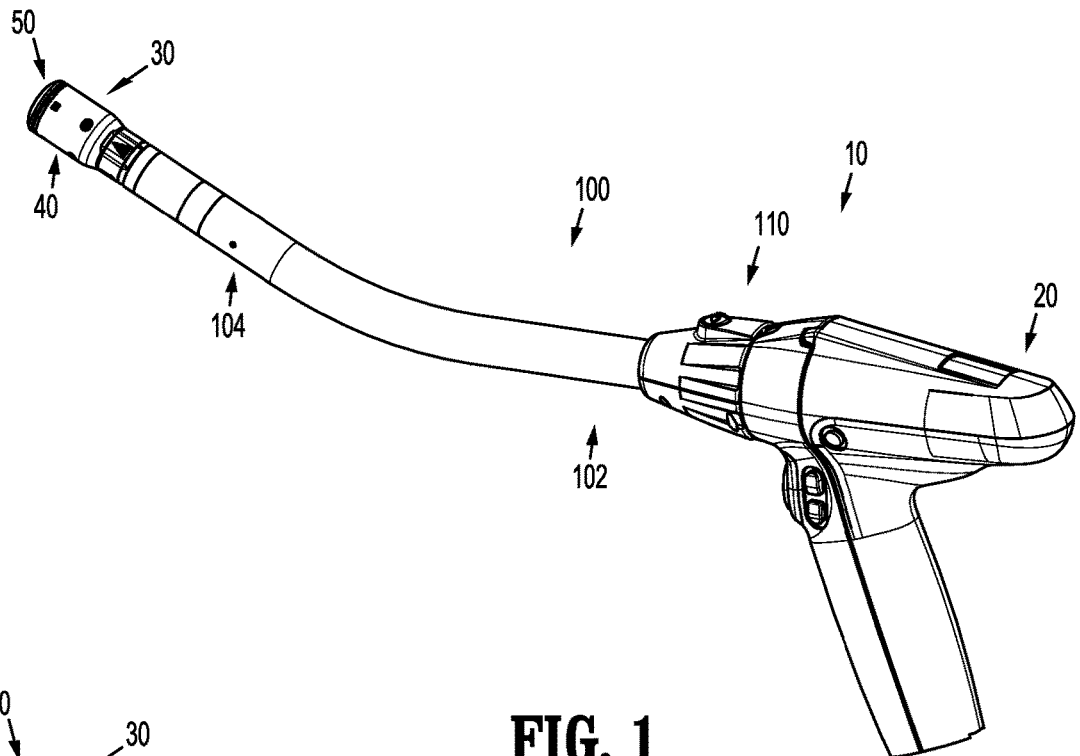
FIG. 1 is a perspective view of a surgical stapling instrument including a handle assembly, an adapter assembly, and an end effector.

Embodiments of the presently disclosed lockout mechanisms will now be described in detail with reference to the drawings in which like reference numerals designate identical or corresponding elements in each of the several views. As is common in the art, the term "proximal" refers to that part or component closer to the user or operator, e.g. surgeon or clinician, while the term "distal" refers to that part or component farther away from the user.

Figure 2:
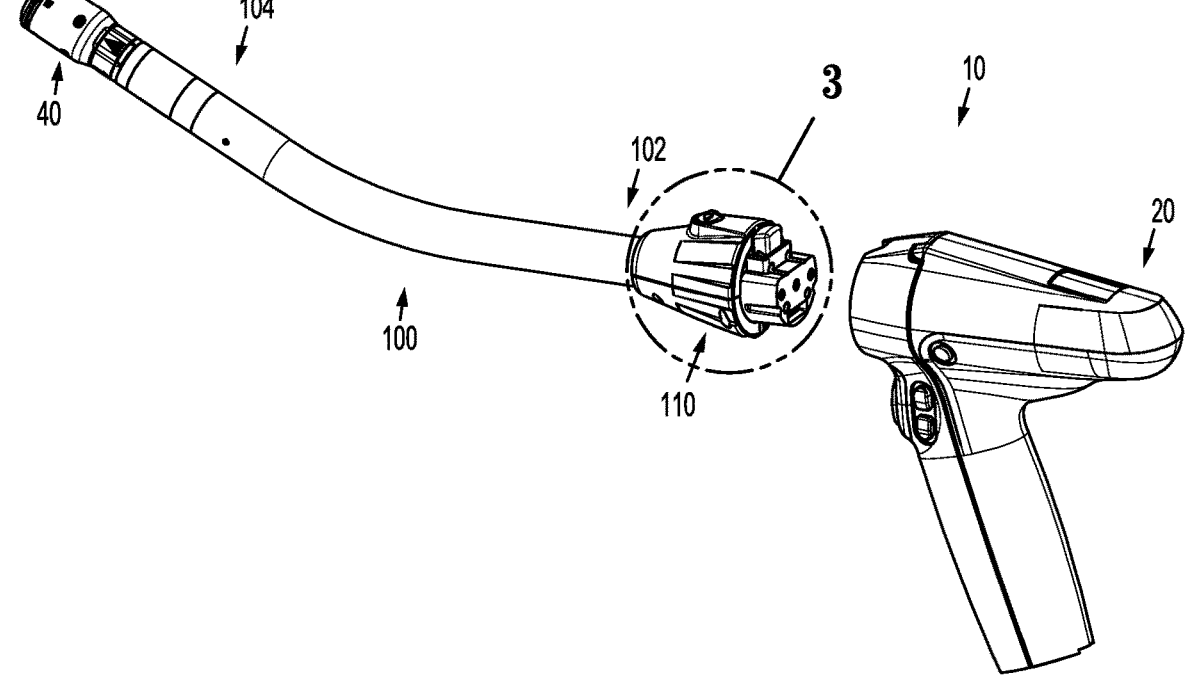
FIG. 2 is a perspective view of the surgical stapling instrument shown in FIG. 1, with the adapter assembly separated from the handle assembly.

Referring initially to FIGS. 1 and 2, an adapter assembly including a lockout mechanism according to an embodiment of the present disclosure, shown generally as adapter assembly 100, is a component of a surgical stapling instrument 10. The surgical stapling instrument 10 further includes a powered handle assembly 20, and an end effector 30. As shown, the end effector 30 includes a loading unit 40, and an anvil assembly 50. Although shown and described with reference to surgical stapling instrument 10, the aspects of the present disclosure may be modified for use with surgical instruments having one or more drive assemblies for effecting actuation of an end effector. For a detailed description of exemplary powered surgical stapling instruments, please refer to commonly owned U.S. Pat. Nos. 9,023,014 and 9,055,943 ("the '014 patent" and "the '943 patent", respectively), the contents of each of which are incorporated by reference herein in their entirety.

The adapter assembly 100 of the surgical stapling instrument 10 will only be described to the extent necessary to fully disclose the aspects of the present disclosure. For a detailed description of exemplary adapter assemblies, please refer to commonly owned U.S. Pat. App. Pub. Nos. 2015/0157321 ("the '321 publication), 2016/0106406 ("the '406 publication"), and 2017/0086879 ("the '879 publication"), the contents of each of which are incorporated by reference herein in their entirety.

With continued reference to FIGS. 1 and 2, the adapter assembly 100 includes a proximal portion 102 configured for operable connection to the handle assembly 20 (FIG. 1) and a distal portion 104 configured for operable connection to the loading unit 30 (FIG. 1). Although shown and described as forming an integral unit, it is envisioned that the proximal and distal portions 102, 104 may be formed as separate units that are releasably securable to one another.

Figure 3:
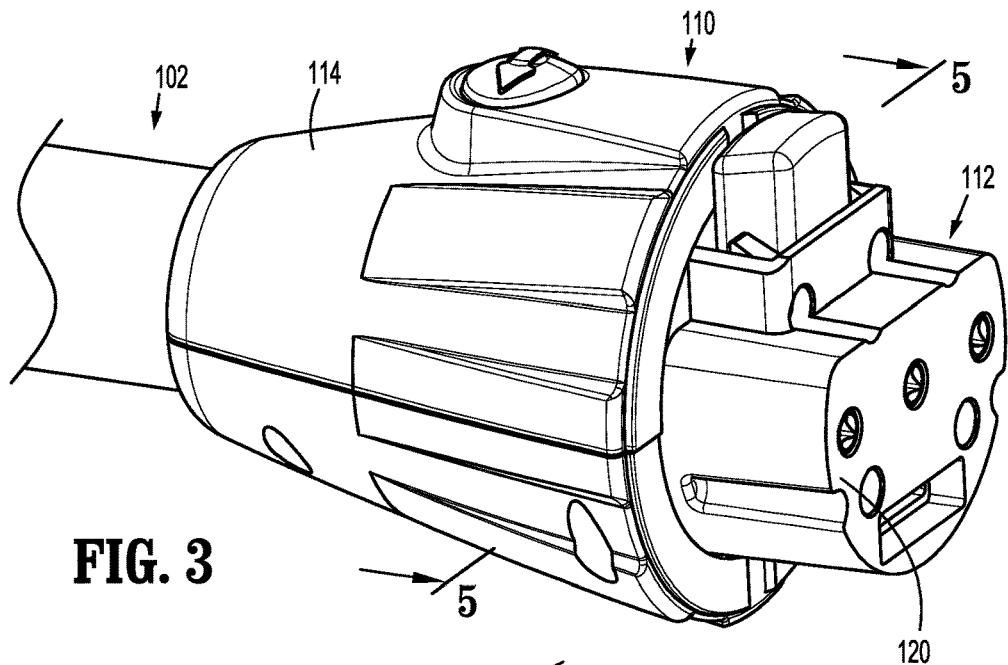
FIG. 3 is a perspective view of a proximal portion of the adapter assembly shown in FIG. 1, including a rotation knob assembly.
Figure 4:
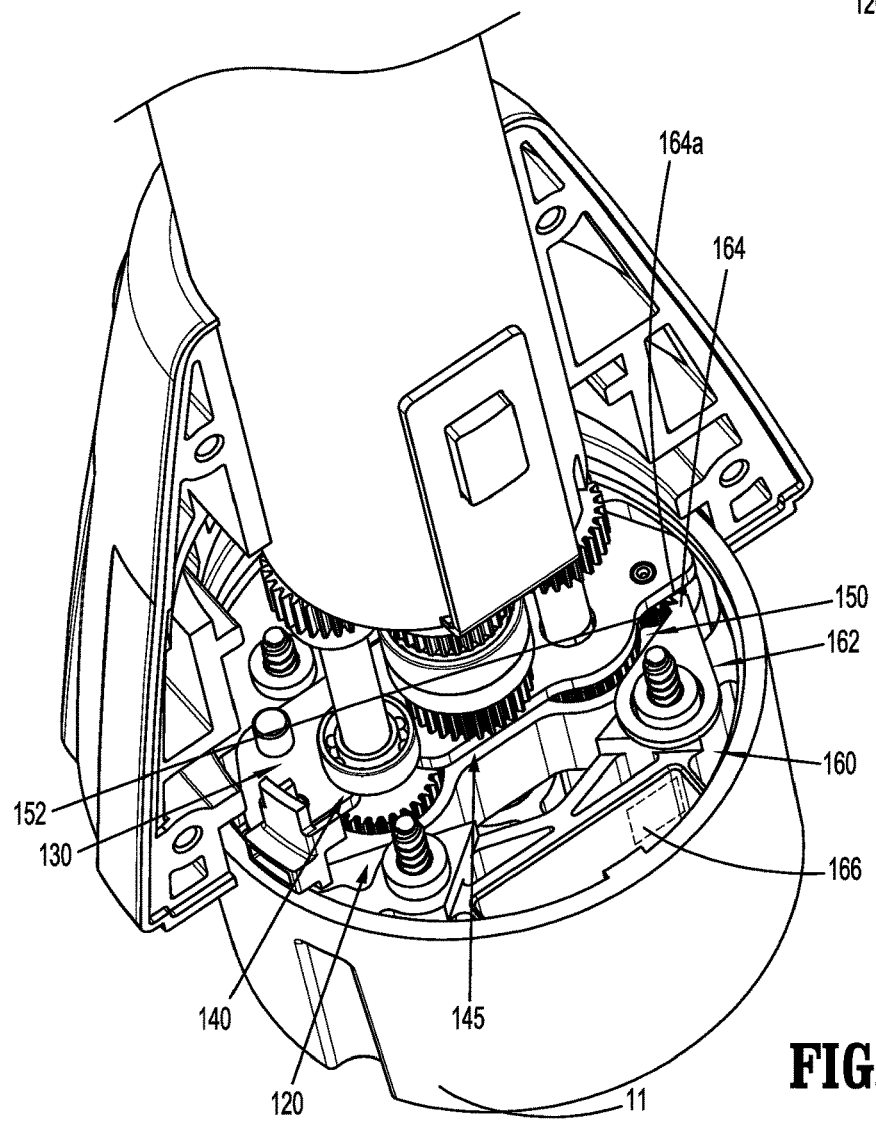
FIG. 4 is a perspective view of the rotation knob assembly shown in FIG. 3, with a housing half of the rotation knob assembly removed.

With reference to FIGS. 3 and 4, the proximal portion 102 of the adapter assembly 100 includes a rotation knob assembly 110. The rotation knob assembly 110 includes a base 112, and a rotation knob 114 rotatably secured to the base 112. The base 112 is configured to operably connect the adapter assembly 100 with the handle assembly 20.

With particular reference to FIG. 4, a drive coupling assembly 120 is operably disposed within the base 112 of the rotation knob assembly 110. The drive coupling assembly 120 engages first, second and third drive shafts (not shown) of the handle assembly 20 (FIG. 1). A drive transfer assembly 130 is disposed within the rotation knob 114 of the rotation knob assembly 110 and is operably secured to the drive coupling assembly 120. The drive coupling assembly 120 and drive transfer assembly 130 remain rotationally fixed relative to the handle assembly to which adapter assembly 100 is attached, e.g., handle assembly 20.

The drive coupling assembly 120 and the drive transfer assembly 130 together form first, second, and third drive assemblies 140, 145, 150. The first, second, and third drive assemblies 140, 145, 150 may each effect a different operation of an attached end effector, e.g., end effector 30 (FIG. 1). For example, the first drive assembly 140 may effect tissue stapling, the second drive assembly 145 may effect tissue cutting, and the third drive assembly 150 may effect tissue clamping.

Figure 5:
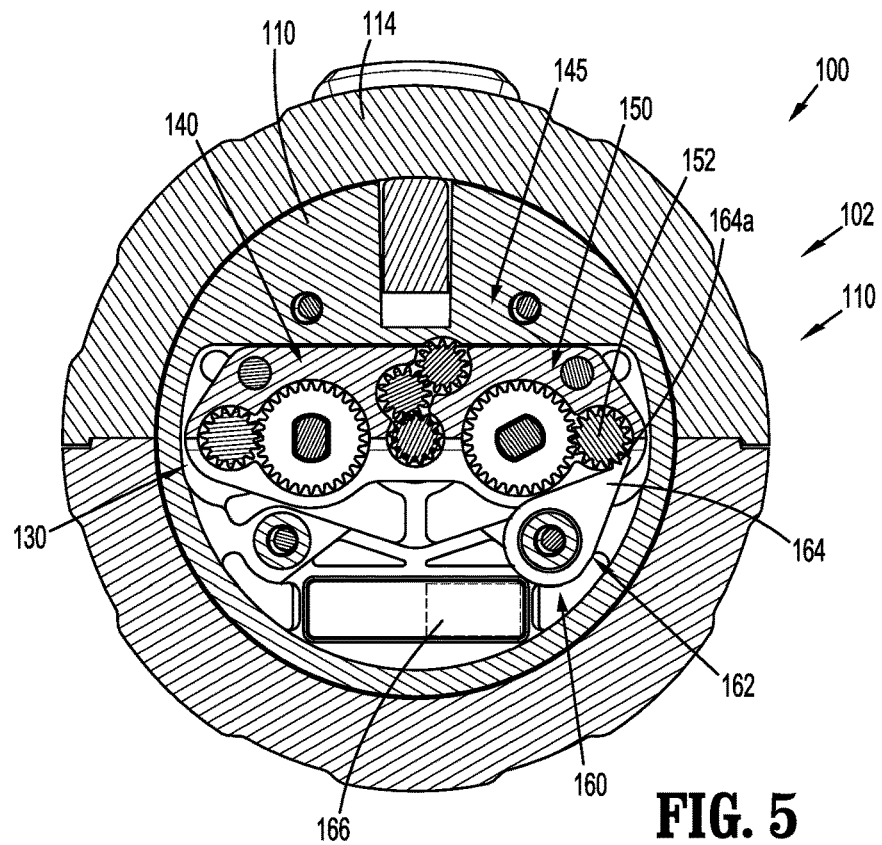
FIG. 5 is a cross-sectional end view taken along line 5-5 shown in FIG. 3, with a lockout mechanism in a locked condition.

With particular reference to FIG. 5, in one embodiment of the present disclosure, a lockout mechanism 160 includes a pawl 162 operably disposed within the rotation knob assembly 110 of the adapter assembly 100. The pawl 162 is pivotally supported relative to a first drive gear 152 of the third drive assembly 150. The pawl 162 includes a plurality of teeth 164a on a free end 164. The plurality of teeth 164a is configured to engage the first drive gear 152 of the third drive assembly 150. In embodiments, and as shown, the plurality of teeth 164a of the pawl 162 is configured to inhibit rotation of the first drive gear 152 in a first direction, e.g., clockwise, and permit rotation of the first drive gear 152 in a second direction, e.g., counter-clockwise. In this manner, the lockout mechanism 160 may permit retraction of the third drive assembly 150 while preventing advancement of the third drive assembly 150. Alternatively, the plurality of teeth 164a of the pawl 162 may be configured to inhibit rotation of the first drive gear 152 in both the first and second directions.

Although shown and described with the pawl 162 in engagement with the first drive gear 152 of the third drive assembly 150, it is envisioned that the lockout mechanism 160 may be modified to include one or more pawls that engage any of the gears of any combination of the first, second, and third drive assemblies 140, 145, 150.

Figure 6:
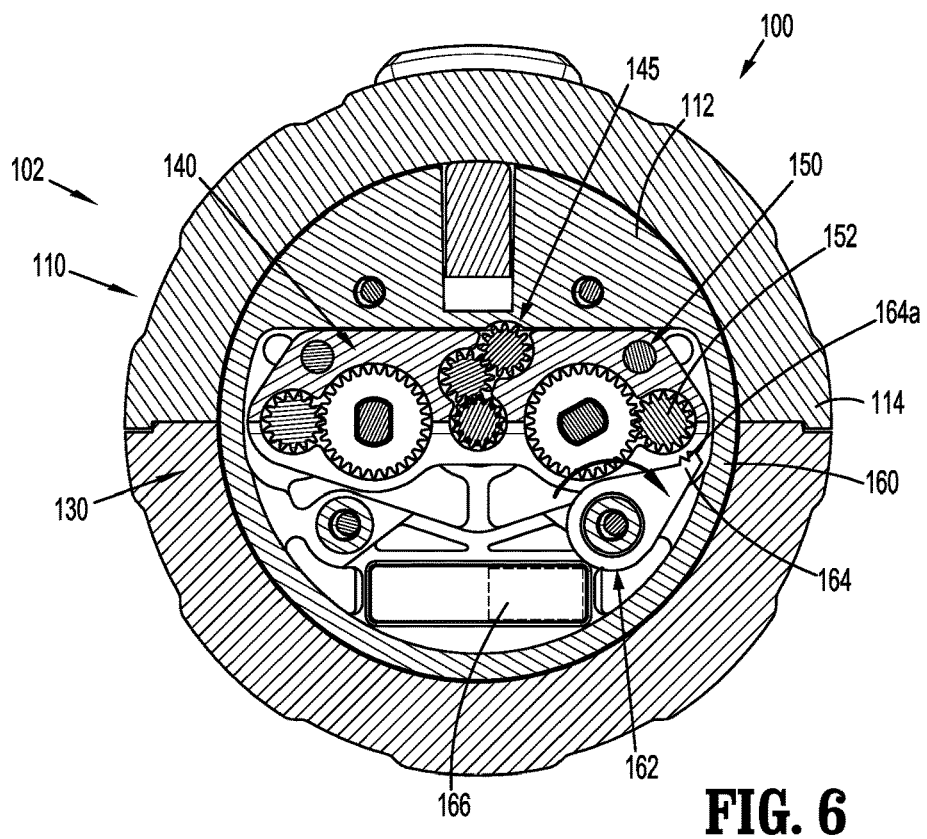
FIG. 6 is a cross-sectional end view taken along line 5-5 shown in FIG. 3, with the lockout mechanism in an unlocked condition.

Turning to FIG. 6, when the handle assembly 20 (FIG. 1) of the surgical stapling instrument 10 is programmed to detect if certain parameters are satisfied, e.g., proper loading of a trocar assembly 170 within the adapter assembly 100, and when satisfied, the handle assembly 20 activates the lockout mechanism 160 to disengage the pawl 162 from the first drive gear 152 of the third drive assembly 150 to permit rotation of the first drive gear 152. In embodiments, the lockout mechanism 160 includes an actuator 166, e.g., a motor, servo, electromagnet or other suitable means for pivoting the pawl 162 out of engagement with the first drive gear 152. Once the pawl 162 disengages from the first drive gear 152, the third drive assembly 150 operates in a traditional manner.

The handle assembly 20 may be programmed to reengage the pawl 162 of the lockout mechanism 160 with the first drive gear 152 of the third drive assembly 150 subsequent to firing of the surgical stapling instrument 10 to prevent reuse of the surgical stapling instrument 10. Similarly, the and/or at any time during the stapling procedure when locking of the third drive assembly 150 may become desired, e.g., malfunction of the surgical stapling instrument 10 (FIG. 1).

Figure 7:
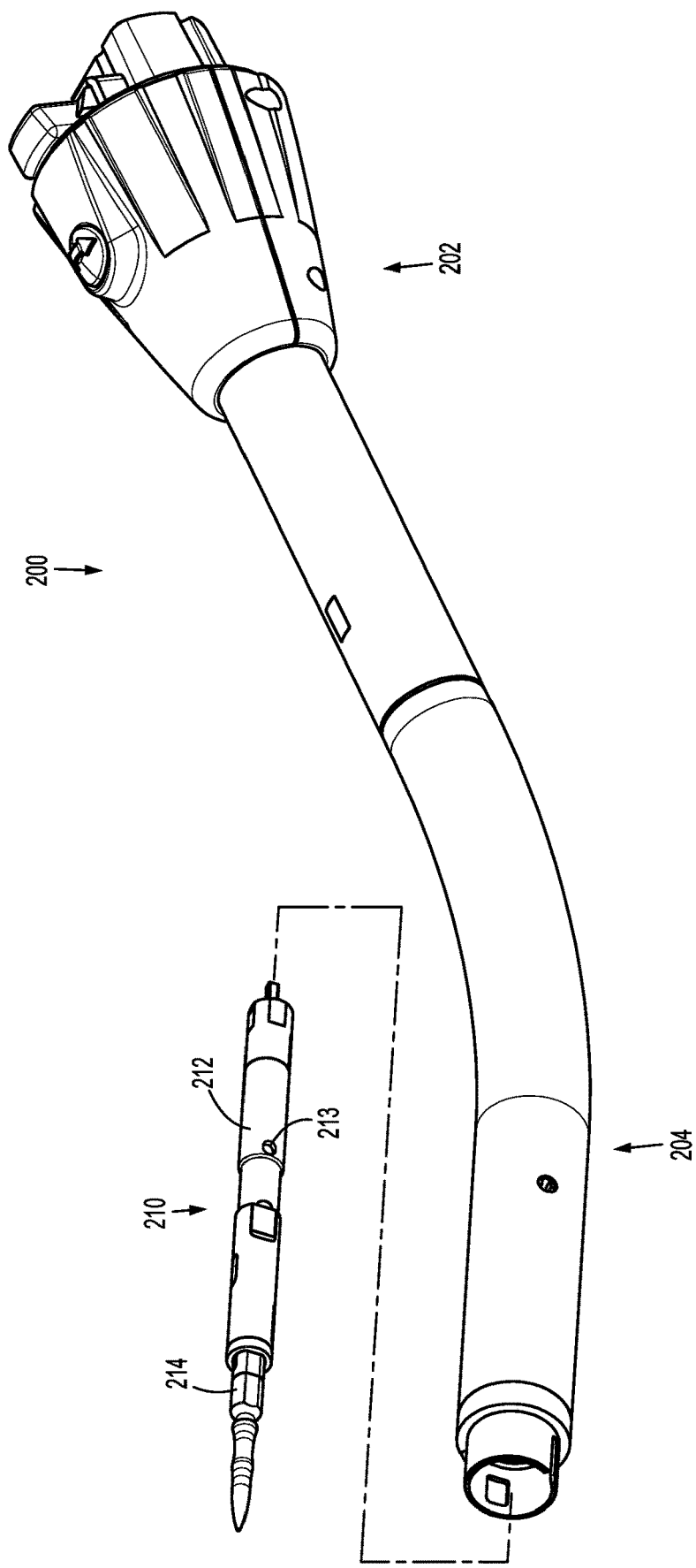
FIG. 7 is a perspective side view of an adapter assembly including a removable trocar.

With reference now to FIG. 7, a lockout mechanism according to another embodiment of the present disclosure will be shown and described with reference to an adapter assembly 200, and a removable trocar assembly 210 releasably disposable within a distal portion 204 of the adapter assembly 200. The adapter assembly 200 is substantially similar to adapter assembly 100 described hereinabove, and will only be described in detail as relates to the differences therebetween.

Figure 13:
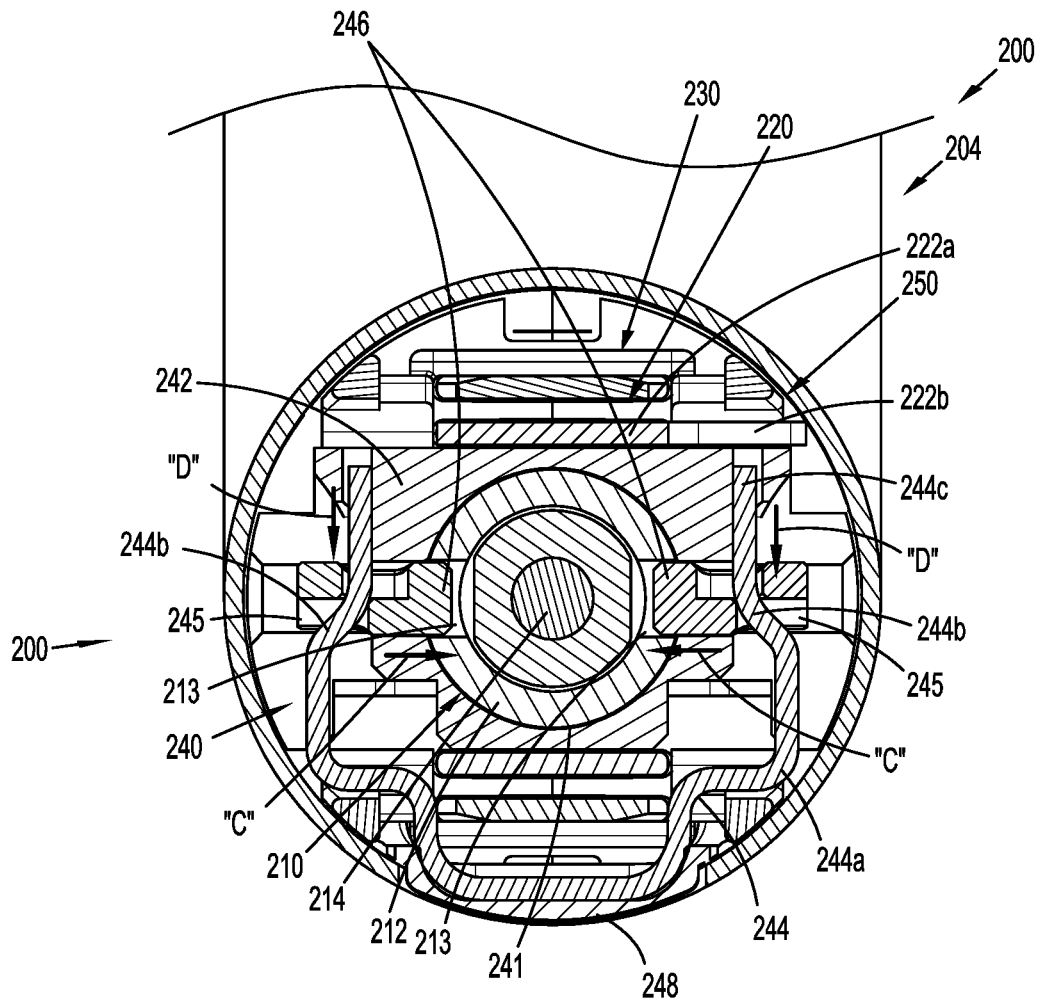
FIG. 13 is a cross-sectional end view taken along line 13-13 shown in FIG. 12, with the lockout mechanism shown in FIG. 8.

The trocar assembly 210 includes a housing 212 and a trocar member 214 selectively extendable from the housing 212. The housing 212 defines a pair of openings 213 (FIG. 13). As will be described in further detail below, the housing 212 of the trocar assembly 210 is configured to be engaged by a retaining mechanism 240 when the trocar assembly 210 is fully received and seated within the distal portion 204 of the adapter assembly 200 to secure the trocar assembly 210 within the adapter assembly 200.

Figure 8:
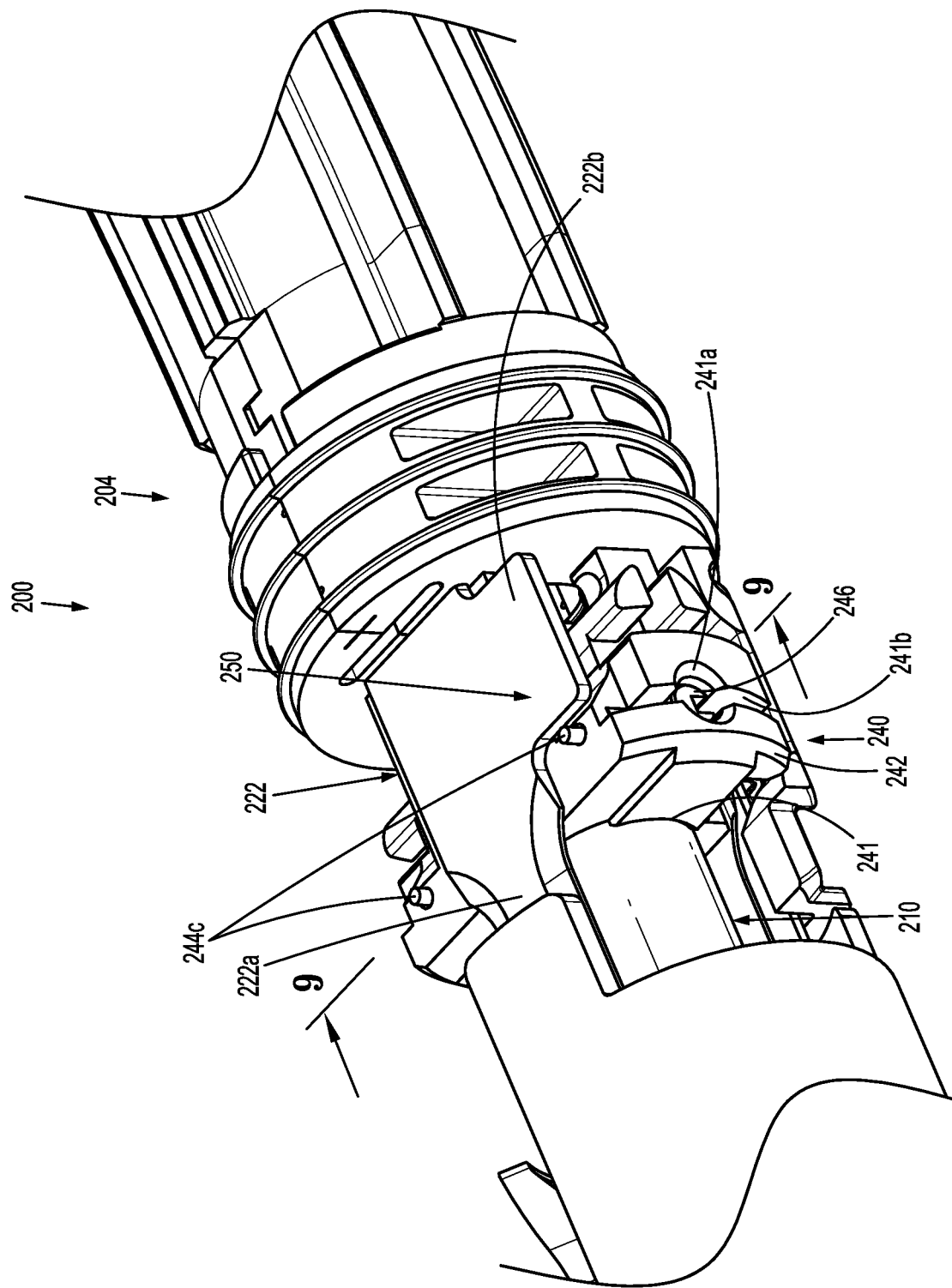
FIG. 8 is a perspective side view of a retaining mechanism and a lockout mechanism of the adapter assembly shown in FIG. 7, with the lockout mechanism in a locked position.
Figure 9:
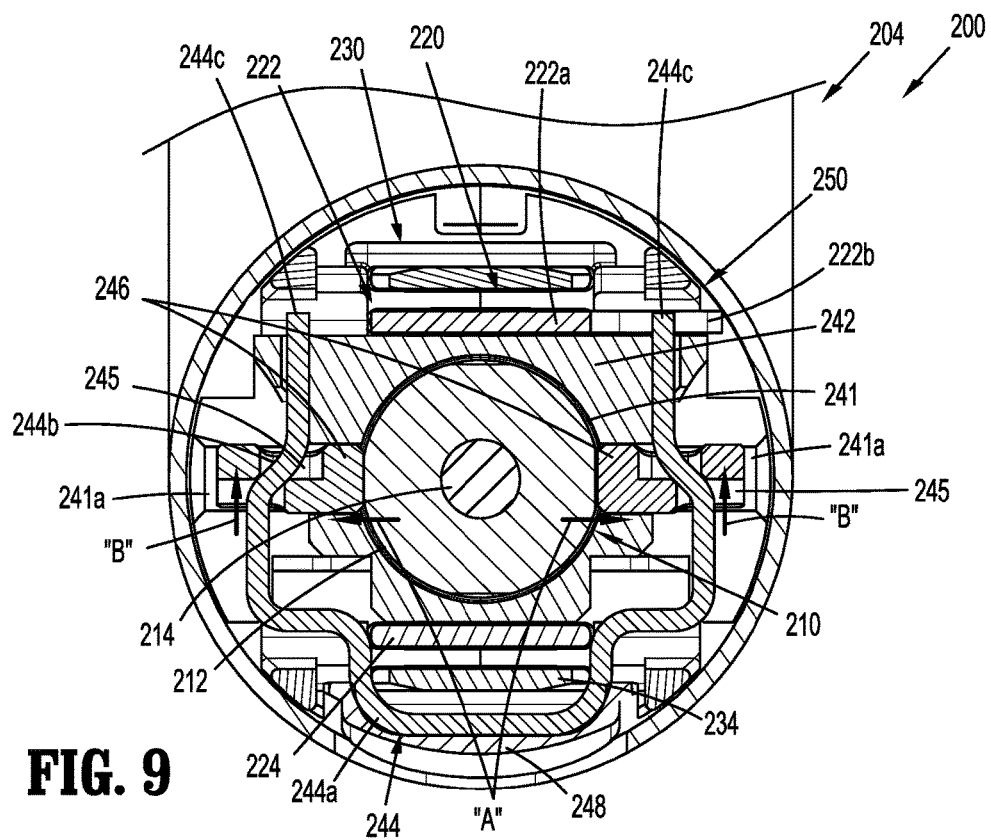
FIG. 9 is a cross-sectional end view taken along line 9-9 shown in FIG. 7, with the lockout mechanism shown in FIG. 8.

With reference now to FIGS. 8 and 9, the retaining mechanism 240 of the adapter assembly 200 is disposed between first and second drive members 222, 224, 232, 234 of respective first and second drive assemblies 220, 230. The first and second drive assemblies 220, 230 are operably connected to first and second drive members (not shown) in a proximal portion 202 of the adapter assembly 200 for effecting operation of an end effector, e.g., the end effector 30 (FIG. 1), to perform first and second functions. More particularly, the first and second drive members 222, 224, 232, 234 of the respective first and second drive assemblies 220, 230 are configured for longitudinal movement within the distal portion 204 of the adapter assembly 200. In embodiments, advancement of the first drive assembly 220 effects tissue stapling, and advancement of the second drive assembly 230 effects tissue cutting.

The first and second drive assemblies 220, 230 will only be described to the extent necessary to fully disclose the aspects of the present disclosure. For a detailed description of exemplary drive assemblies, please refer to the '879 publication, the content of which was previously incorporated herein.

Figure 10:
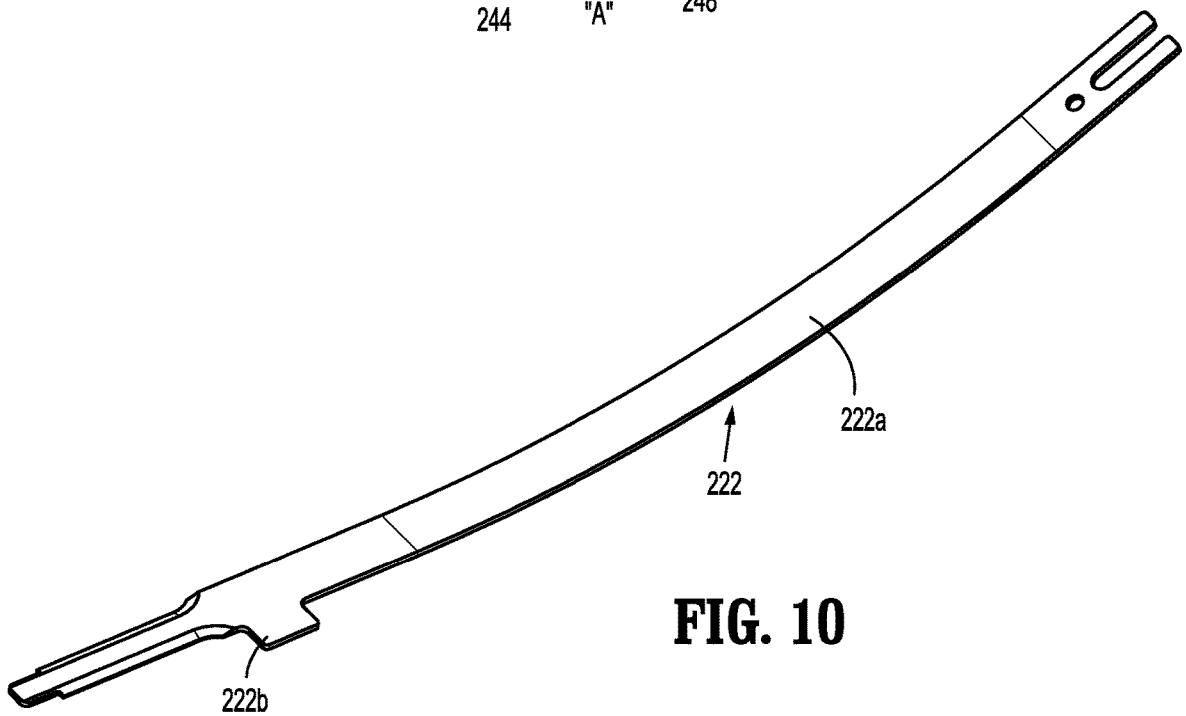
FIG. 10 is a perspective view of a drive member of the adapter assembly shown in FIG. 7.

With additional reference to FIG. 10, the first drive member 222 of the first drive assembly 220 includes an elongate band 222a and a flange portion 222b extending outwardly from a proximal portion of the elongate band 222a. As will be described in further detail below, the flange portion 222b of the first drive member 222 is configured to be engaged by a wire cam or spring clip 244 of a lockout mechanism 250 to inhibit advancement of the first drive assembly 220 when the trocar assembly 210 is not fully received and seated within the adapter assembly 200.

Figure 11:
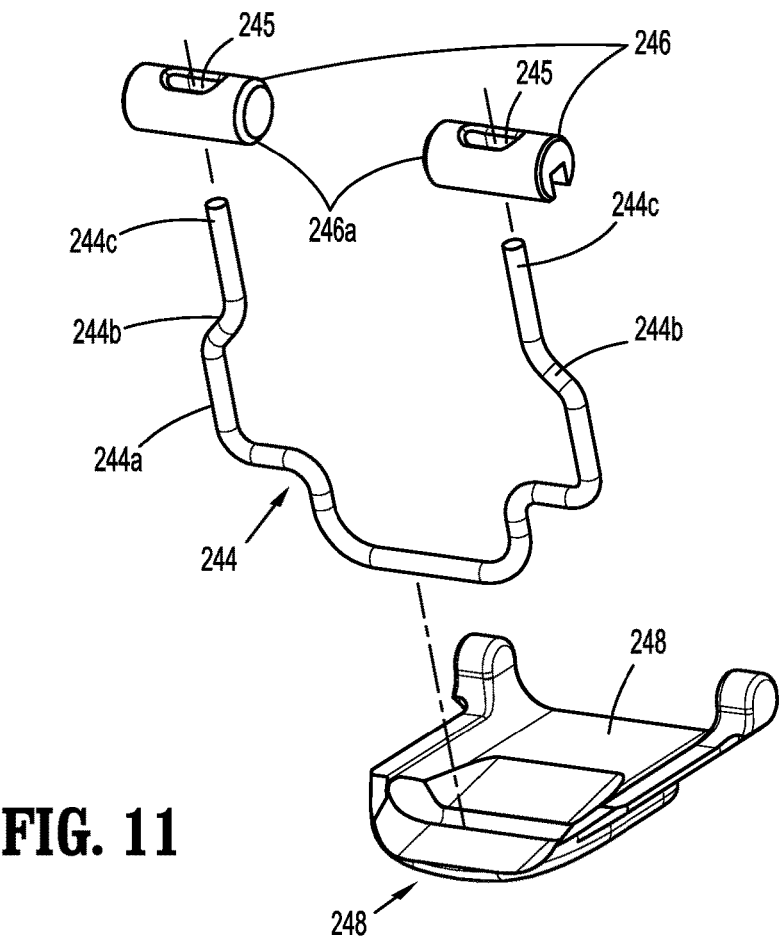
FIG. 11 is a perspective view of the wire cam, retaining members, and a release button of the lockout mechanism shown in FIG. 8.

With continued reference to FIGS. 8 and 9, and additional reference to FIG. 11, the retaining mechanism 240 of the adapter assembly 200 includes a retaining block 242, a wire cam 244 (FIG. 9), a pair of retaining members 246 (FIG. 9), and a release button 248 (FIG. 11). The retaining block 242 of the retaining mechanism 240 defines a central opening 241 for receiving the trocar assembly 210, a pair of opposed cylindrical openings 241a in communication with the central opening 241 for receiving the retainer members 246, and a channel or slot 241b extending about a perimeter of the retaining block 242 and through the cylindrical openings 241a in the retaining block 242 for receiving the wire cam 244. The retainer members 246 of the retaining mechanism 240 are supported within the cylindrical openings 241a by the wire cam 244 and are configured to be received within the openings 213 (FIG. 9) in the housing 212 of the trocar assembly 210 when the trocar assembly 210 is fully received and seated within the distal portion 204 of the adapter assembly 200.

The wire cam 244 of the retaining mechanism 240 includes a substantially U-shaped body 244a having a pair of opposed angled sections 244b and free ends 244c. The wire cam 244 is received within the channel 241b of the retaining block 242 and is moveable between a first position (FIG. 9) when the trocar assembly 210 is partially received within the distal portion 204 of the adapter assembly 200, e.g., the retaining members 246 are not aligned with the openings 213 in the housing 212 of the trocar assembly 200, and a second position (FIG. 13) when the trocar assembly 210 is fully received within the distal portion 204 of the adapter assembly 200, e.g., the retaining members 246 are aligned with and received in the openings 213 in the housing 212.

With particular reference to FIGS. 8 and 9, when the wire cam 244 of the retaining mechanism 240 is in the first position, the free ends 244c of the wire cam 244 extend beyond the retainer block 242 of the retaining mechanism 240. The first drive member 222 of the first drive assembly 220 and the retaining block 242 of the retaining assembly 240 are configured such that one of the free ends 244c of the wire cam 244 of the retainer assembly 240 engages the flange 222b of the first drive member 222 to form the lockout mechanism 250. The lockout mechanism 250 inhibits operation of the first drive assembly 220, e.g., advancement of the first drive member 222. Although shown with only one of the free ends 244c of the wire cam 244 engaging the first drive member 222 of the first drive assembly 220, it is envisioned that the first drive member 222 may be configured to engage both free ends 244c of the wire cam 244. In embodiments, the engagement of the first drive member 222 of the first drive assembly 220 with the flange 222b of the first drive member 222 provides sufficient resistance to movement that the handle assembly 20 (FIG. 1)

detects and identifies that the trocar assembly 210 is not fully received and properly seated within the adapter assembly 200.

The retaining members 246 of the retaining mechanism 240 are supported on the angled portions 244b of the wire cam 244. The retaining members 246 may include an inclined inner surface 246a (FIG. 11) to facilitate receipt of the trocar assembly 210 therebetween. The retaining members 246 each define an opening 245 through which the respective angled section 244b of the wire cam 244 is received. The wire cam 244 and the retaining members 246 are configured such that when the trocar assembly 210 is not fully received within the distal portion 204 of the adapter assembly 200, the wire cam 244 is maintained in the first position (FIG. 9), with the free ends 244c of the wire cam 244 extending beyond the retaining block 242. In this manner, at least one of the free ends 244c of the wire cam 244 engages the first drive member 222 of the first drive assembly 220 to inhibit advancement of the first drive member 222.

As shown in FIGS. 8 and 9, when the trocar assembly 210 is received within the distal portion 204 of the adapter assembly 200 and when the openings 213 in the housing 212 of the adapter assembly 200 are not aligned with the retaining members 246, the housing 212 of the trocar assembly 210 biases the retaining members 246 outward, as indicated by arrows "A" in FIG. 9. The angled sections 244c of the wire cam 244 and the openings 245 in the retaining members 246 are configured such that when the retaining members 246 are biased outwardly through contact with the housing 212 of the trocar assembly 210, the cam wire 244 is biased upwardly, as indicated by arrows "B" in FIG. 9, to cause the free ends 244c of the cam wire 244 to extend beyond the retaining block 242 and into the path of the first drive member 222 of the first drive assembly 220.

Figure 12:
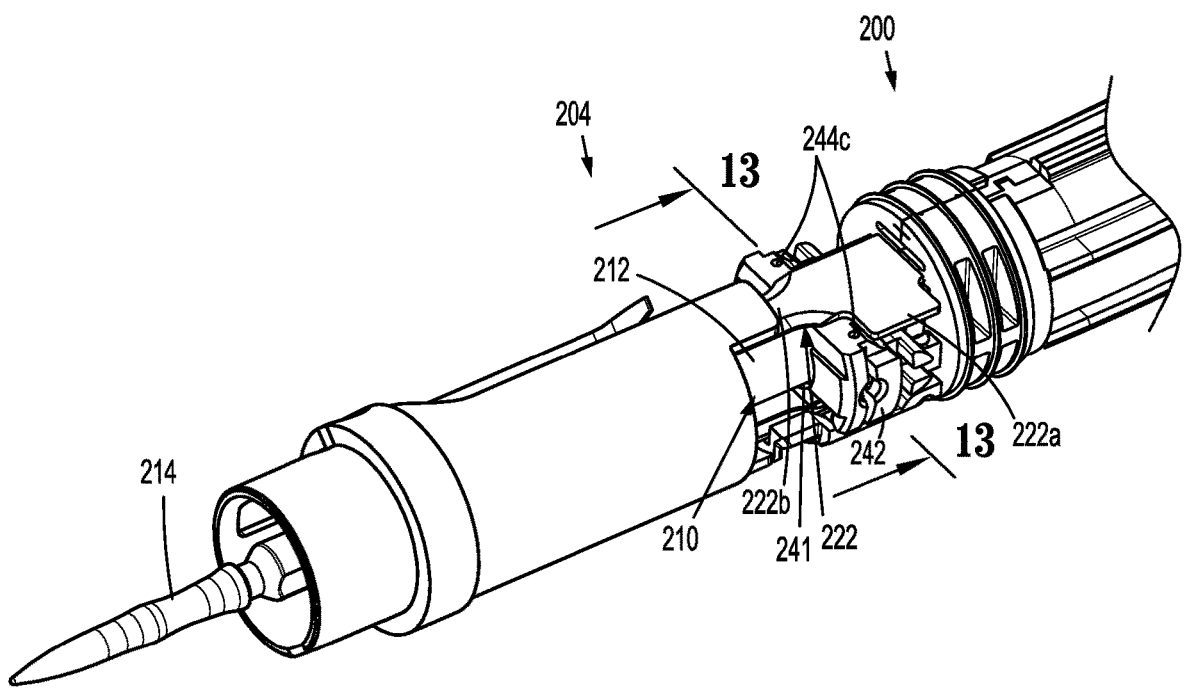
FIG. 12 is a perspective side view of the retaining mechanism and the lockout mechanism shown in FIG. 7, with the lockout mechanism in an unlocked position.

With reference to FIGS. 12 and 13, when the trocar assembly 210 is fully received and properly seated within the distal portion 204 of the adapter assembly 200 (FIG. 13), e.g., the openings 213 of the housing 212 of the trocar assembly 210 are aligned with the retaining members 246 of the retaining mechanism 240, the retaining members 246 move within the openings 213 in the housing 212 of the trocar assembly 210, as indicated by arrows "C" in FIG. 13. Movement of the retaining members 246 into the openings 213 of the housing 212 moves the cam wire 244 downwardly (as illustrated in FIG. 9) such that the free ends 244c of the cam wire 244 are retracted within the retaining block 242. Retraction of the free ends 244c of the cam wire 244 within the retaining block 242 clears a path for the first drive member 222 of the first drive assembly 220. The adapter assembly 200 then operates in a traditional manner.

Following a stapling procedure with adapter assembly 200, the trocar assembly 210 may be released from the adapter assembly 200 by pressing the retaining button 248 of the retaining mechanism 240 to cause the cam wire 244 to move upwardly (as illustrated in FIG. 9) and result in the retaining members 246 moving outwardly from within the openings 213 in the housing 212 of the trocar assembly 210. Once the retaining members 246 clear the openings 213 in the housing 212, the trocar assembly 210 may be removed from within the distal portion 204 of the adapter assembly 200.

With reference now to FIGS. 14-16, another lockout mechanism according to the present disclosure is shown generally as lockout mechanism 300. As shown, the lockout mechanism 300 is configured to inhibit advancement of a drive member 312 of a drive assembly 310. More particularly, the lockout mechanism 300 includes a locking member 302 that is pivotally secured relative to the drive member 312. The locking member 302 is configured to be received within a cutout 313 in the first drive member 312. The cutout 313 is defined by a vertical distal facing surface 314a and a sloped proximal facing surface 314b. When the locking member 302 is received within the cutout 313 and in engagement with the vertical distal facing surface 314a, the locking member 302 inhibits movement of the drive member 312.

The lockout mechanism 300 further includes an electromagnet 304 disposed adjacent the locking member 302. When activated, the electromagnet 304 causes the locking member 302 to pivot out of the cutout 313 in the drive member 312, thereby permitting advancement of the drive member 312. Although shown as including an electromagnet 304, it is envisioned that the locking member 302 may be moved with a motor, solenoid, or other mechanism. Although shown as being pivoted out of engagement with the drive member 312, it is envisioned that the locking member 302 may instead by retracted or otherwise moved in a linear manner from within the cutout 313.

With particular reference to FIG. 16, a distance "x" between the vertical distal facing surface 314a of the drive member 312 and the sloped proximal facing surface 314b of the drive member 312 determines the distance the drive member 312 may be advanced before the lockout mechanism 300 engages. The greater the distance "x", the greater the distance the drive member 312 may be advanced prior to the lockout mechanism 300 engaging.

Figure 18:
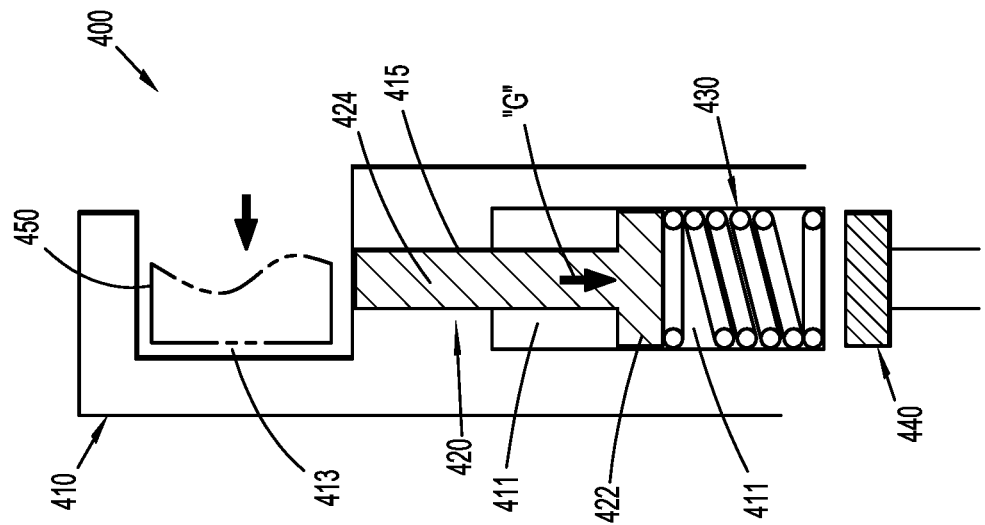
FIG. 18 is a partial cross-sectional side view of the lockout mechanism shown in FIG. 18, with the plunger member in an unlocked position.
Figure 17:
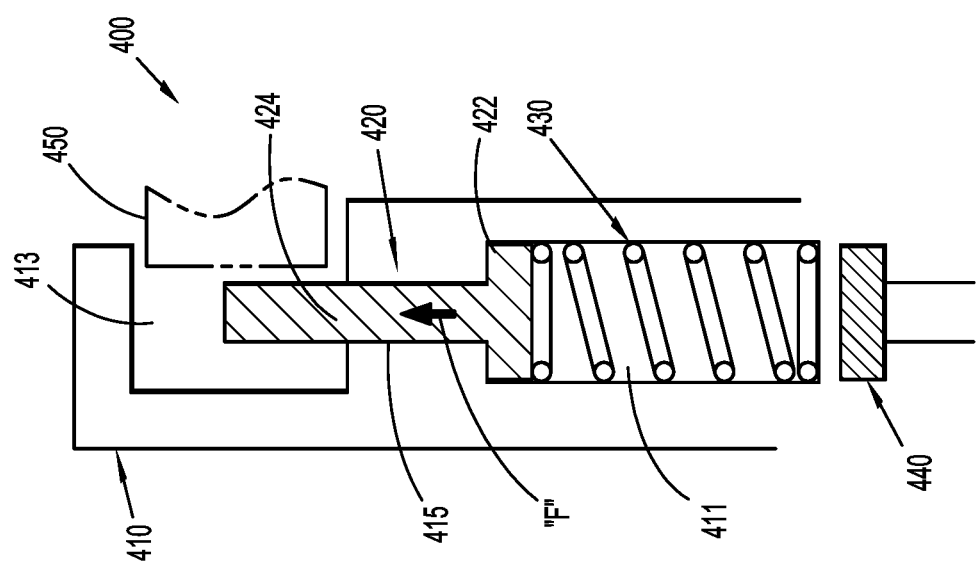
FIG. 17 is a partial cross-sectional side view of a lockout mechanism according to another embodiment of the present disclosure, with a plunger member in a locked position.

Turning to FIGS. 17 and 18, another lockout mechanism according to the present disclosure is shown generally as lockout mechanism 400. The lockout mechanism 400 includes a housing 410, a plunger member 420, a biasing member, e.g., spring 430, and an electromagnet 440. Although shown including a housing 410, it is envisioned that the lockout mechanism 400 may be incorporated directly into an adapter assembly, e.g., adapter assembly 100.

The housing 410 of the locking mechanism 400 includes a cylindrical recess 411, a cutout 413, and a passage 415 extending between the cylindrical recess 411 and the cutout 413. The plunger member 420 includes a head portion 422 and an elongate body portion 424. The head portion 422 is received within the cylindrical recess 411 and the elongate body portion 424 extends through the passage 415 into the cutout 413. The biasing member, e.g., spring 430, is disposed within the cylindrical recess 411 and biases the plunger member 420 in a first direction, as indicated by arrow "F" in FIG. 17, into an extended or locked position. In the locked position, the elongate body portion 424 of the plunger member 420 extends from the passage 415 into the cutout 413.

The electromagnet 440 is disposed adjacent the cylindrical recess 411 opposite the passage 415. Activation of the electromagnet 440 retracts the plunger member 420 against the bias of the spring 430, as indicated by arrow "G" in FIG. 18, into a retracted or unlocked position. When the plunger member 420 is in the unlocked position, the elongate body portion 424 of the plunger member 420 is retracted from within the cutout 413 of the housing 410 of the locking mechanism 400 such that the cutout is unobstructed.

In operation, the locking mechanism 400 is positioned within a surgical instrument, e.g., surgical stapling instrument 10 (FIG. 1), such that the cutout 413 of the housing 410 is in alignment with a path (not shown) of a drive member (not shown) or connecting element 450. When the plunger member 420 is in the locked position, the elongate body portion 424 of the plunger member 420 is disposed within the cutout 413, thereby obstructing the path of the drive member and/or connector member 450 and preventing advancement of the drive member through the housing 410 of the locking mechanism 400 and/or connection of the connector member 450 with the housing 410.

As noted above, activation of the electromagnet 440 causes the plunger member 420 to retract to the unlocked position (FIG. 18), thereby clearing the path through the cutout 413 in the housing 410. In this manner, the drive member (not shown) is able to pass through the housing 410 unobstructed. Similarly, the connector member 450 is able to be received within the cutout 413 in the housing 410 of the locking mechanism 400 to secure the connector member 450 with the housing 410.

Figure 20:
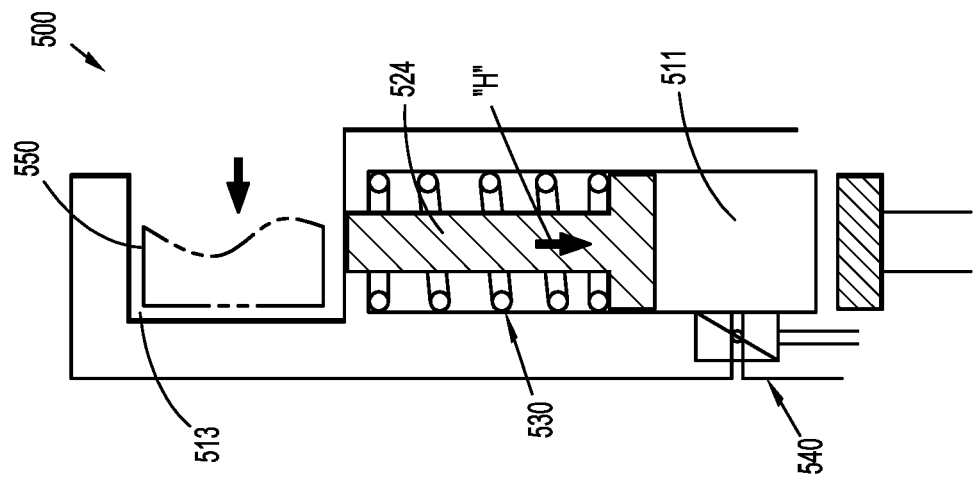
FIG. 20 is a partial cross-sectional side view of the lockout mechanism shown in FIG. 19, with the plunger member in an unlocked position.
Figure 19:
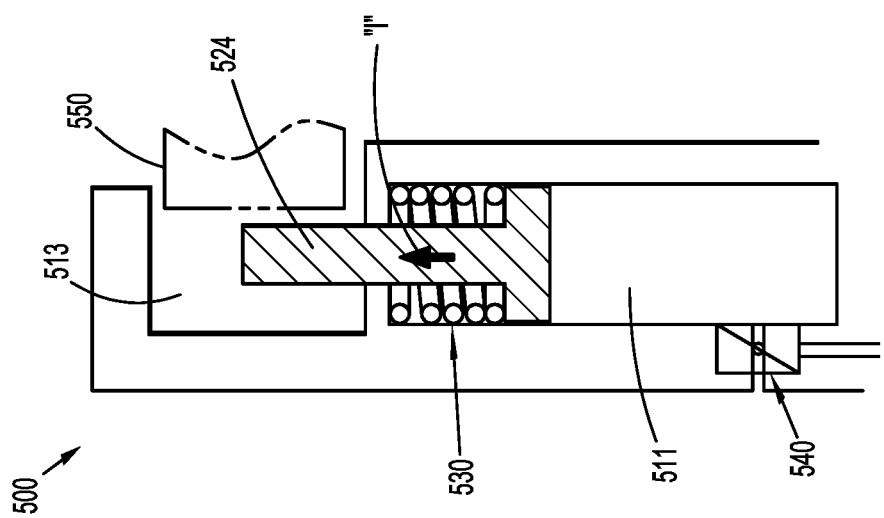
FIG. 19 is a partial cross-sectional side view of a lockout mechanism according to another embodiment of the present disclosure, with a plunger member in a locked position.

With reference now to FIGS. 19 and 20, a locking mechanism according to another embodiment of the present disclosure is shown generally as locking mechanism 500. The locking mechanism 500 is substantially similar to locking mechanism 400 described hereinabove, and will only be described in detail as relates to the difference therebetween.

In the locking mechanism 500, a plunger member 520 is maintained in a retracted or unlocked position (FIG. 20) within a cylindrical recess 511 of a housing 510 by a biasing member, e.g., spring 530, as indicated by arrow "G" in FIG. 20. When in the unlocked position, an elongate body portion 524 of the plunger member 520 obstructs a cutout 513 in the housing 510 to prevent advancement of a drive member (not shown) and/or preventing receipt of a connector member 550 within the cutout 513.

The locking mechanism 500 includes a pneumatic valve 540 in communication with the cylindrical recess 511. Activation of the pneumatic valve 540 pressurizes the cylindrical recess 511 thereby causing the plunger member 520 to move to an advanced or locked position (FIG. 19) within the cylindrical recess 511, as indicated by arrow "I" in FIG. 19, against the bias of the spring 530. When the in the locked position. The elongate body portion 524 of the plunger member 520 is received within the cutout 513 of the housing 510, thereby obstructing the path of the drive member and/or connection member 550.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described.

The invention claimed is:

1. A surgical instrument comprising:
   a first drive assembly including a first drive gear; and
   a lockout mechanism positioned for releasable engagement with the first drive assembly to inhibit rotation of the first drive gear, the lockout mechanism including a pawl and an actuator for moving the pawl from a first position in engagement with the first drive gear to a second position spaced from the first drive gear.

2. The surgical instrument of claim 1, wherein the pawl includes a plurality of teeth and the first drive gear includes a plurality of teeth, the plurality of teeth of the pawl being in engagement with the plurality of teeth of the first drive gear when the pawl is in the first position.

3. The surgical instrument of claim 1, wherein the pawl pivots from the first position to the second position.

4. The surgical instrument of claim 1, further including an adapter assembly, the first drive assembly and the lockout mechanism being disposed within the adapter assembly.

5. The surgical instrument of claim 4, further including a handle assembly, the adapter assembly being releasably secured to the handle assembly.

6. The surgical instrument of claim 5, further including an end effector releasably secured to the adapter assembly.

7. The surgical instrument of claim 6, wherein the end effector includes a loading unit and an anvil assembly.

8. The surgical instrument of claim 1, wherein the actuator includes a motor, a servo, or an electromagnet.

9. A surgical instrument comprising:
   a first drive assembly including a first drive gear; and
   a lockout mechanism positioned for releasable engagement with the first drive assembly to inhibit rotation of the first drive gear in a first direction, the lockout mechanism including a pawl and an actuator for moving the pawl from a first position in engagement with the first drive gear to a second position spaced from the first drive gear.

10. The surgical instrument of claim 9, wherein the pawl includes a plurality of teeth and the first drive gear includes a plurality of teeth, the plurality of teeth of the pawl being in engagement with the plurality of teeth of the first drive gear when the pawl is in the first position.

11. The surgical instrument of claim 9, wherein the pawl pivots from the first position to the second position.

12. The surgical instrument of claim 9, wherein the actuator includes a motor, a servo, or an electromagnet.

13. The surgical instrument of claim 9, wherein the lockout mechanism inhibits rotation of the first drive gear in a second direction.

14. The surgical instrument of claim 9, further including a handle assembly, an adapter assembly releasably secured to the handle assembly, and an end effector releasably secured to the adapter assembly, wherein the first drive assembly and the lockout mechanism are disposed within the adapter assembly.

15. The surgical instrument of claim 14, wherein the end effector includes a loading unit and an anvil assembly.

16. A surgical instrument comprising:
   a first drive assembly including a first drive gear; and
   a lockout mechanism positioned for releasable engagement with the first drive assembly to inhibit rotation of the first drive gear, the lockout mechanism including a pawl and an actuator for moving the pawl from a first position in engagement with the first drive gear to a second position spaced from the first drive gear, the actuator including a servo.

17. The surgical instrument of claim 16, wherein the pawl includes a plurality of teeth and the first drive gear includes a plurality of teeth, the plurality of teeth of the pawl being in engagement with the plurality of teeth of the first drive gear when the pawl is in the first position.

18. The surgical instrument of claim 16, wherein the pawl pivots from the first position to the second position.

19. The surgical instrument of claim 16, further including an adapter assembly, the first drive assembly and the lockout mechanism being disposed within the adapter assembly.

20. The surgical instrument of claim 19, further including a handle assembly and an end effector, the adapter assembly being releasably secured to the handle assembly and the end effector being releasably secured to the adapter assembly.

* * * * *